(12) United States Patent
Maguire, Jr. et al.

(10) Patent No.: US 7,648,023 B2
(45) Date of Patent: Jan. 19, 2010

(54) ENDOSCOPE PRE-CLEAN KIT

(75) Inventors: Walter L. Maguire, Jr., Guilford, CT (US); Shaun Sweeney, Hamburg, NJ (US)

(73) Assignee: Cygnus Medical LLC, Branford, CT (US)

( * ) Notice: Subject to any disclaimer, the term of this patent is extended or adjusted under 35 U.S.C. 154(b) by 350 days.

(21) Appl. No.: 11/412,641

(22) Filed: Apr. 27, 2006

(65) Prior Publication Data

US 2007/0251037 A1 Nov. 1, 2007

(51) Int. Cl.
*B65D 81/24* (2006.01)
(52) U.S. Cl. ............... 206/207; 206/361; 206/438; 206/570; 383/202; 383/209
(58) Field of Classification Search ......... 206/205, 206/210, 216, 223, 570, 572, 438, 207, 361; 15/104.001; 383/33, 59, 66, 121, 200, 202, 383/207–209
See application file for complete search history.

(56) References Cited

U.S. PATENT DOCUMENTS

| 3,255,871 | A | * | 6/1966 | Butler ........................ 206/205 |
|---|---|---|---|---|
| 4,898,477 | A | | 2/1990 | Cox et al. ..................... 383/33 |
| 4,989,733 | A | * | 2/1991 | Patry .......................... 206/570 |
| 5,425,583 | A | | 6/1995 | Wild ........................... 383/202 |
| 5,833,368 | A | | 11/1998 | Kaufman ..................... 383/205 |
| 5,873,656 | A | | 2/1999 | Arkins et al. ................ 383/202 |
| 5,988,371 | A | * | 11/1999 | Paley et al. .................. 206/210 |
| 6,481,889 | B2 | | 11/2002 | Delsahut ...................... 383/44 |
| 2002/0102032 | A1 | * | 8/2002 | Sturgis et al. ............... 383/209 |
| 2003/0128899 | A1 | * | 7/2003 | Dennis ........................ 383/202 |
| 2005/0177964 | A1 | * | 8/2005 | Cisneros ................... 15/104.94 |

\* cited by examiner

*Primary Examiner*—Luan K Bui
(74) *Attorney, Agent, or Firm*—St. Onge Steward Johnston & Reens LLC

(57) ABSTRACT

An endoscope pre-cleaning kit has a sealed, flexible pouch having front and back sidewall panels and a bottom gusset panel. The sidewall panels are superimposed over one another and sealed together proximate to their top and side peripheral edges to define a top seal and two opposing side seals. The sidewall panels are sealed to the bottom gusset panel proximate to their bottom peripheral edges to define a gusseted bottom portion such that the pouch is adapted to stand upright. The kit also includes a pre-diluted detergent contained within the pouch, and an absorbent pad adapted to absorb a portion of the detergent. The pouch includes a portion adapted to be opened in order to access the detergent.

21 Claims, 5 Drawing Sheets

ENDOSCOPE PRE-CLEAN KIT

FIELD OF THE INVENTION

The present invention relates to a cleaning kit for an endoscope, and more particularly, to such a cleaning kit which is particularly well-suited to being used immediately after a procedure in order to clear debris from the channel and insertion tube of the endoscope, and before a more thorough cleaning and/or sterilization is conducted.

BACKGROUND OF THE INVENTION

As is well known, surgical instruments used in the healthcare industry must be cleaned and sterilized before and after each use. Cleaning and sterilization, of course, frees instruments from microorganism contamination, to prevent infections and the spread of diseases among patients. All medical procedures rely upon a stringent program of cleaning and sterilization.

It is common, in the case of endoscopes and similar devices, for cleaning and sterilization to be performed in multiple steps at multiple times. For example, it is common for an initial cleaning to be performed "bedside" immediately after a procedure in order to clear debris from the channel and insertion tube of the endoscope, then for the endoscope to be more thoroughly cleaned and sterilized later.

Generally, this initial cleaning is performed while the endoscope still has suction ability, and involves, first, wiping down the exterior of the endoscope with a sponge or other similar absorbent material soaked in an enzymatic detergent, and then suctioning up a relatively small amount of the enzymatic detergent through the endoscope in order to clear debris from the interior of the endoscope channel. Typically, air and enzymatic detergent are alternated through the channel to enhance the cleaning thereof.

Traditionally, the various elements necessary for performing this initial cleaning were sold separately and assembled by the person performing the cleaning. For example, the enzymatic detergent typically would be sold in concentrated form, such that the person performing the cleaning would have to measure and mix appropriate amounts of the detergent concentrate and water in a suitable container, then locate an appropriate sponge or other absorbent material, and then perform the cleaning described above. Thus, the amount of labor involved with preparing the elements necessary for performing the cleaning was typically greater than the labor involved with the cleaning itself.

More recently, a pre-cleaning kit has been developed which comprises a shallow plastic tray, in which is disposed enzymatic cleaner (in a pre-diluted form) and a sponge. The tray is sized such that only the amount of enzymatic detergent necessary for a single cleaning is included, and the tray includes a pull-away lid sealing the sponge and the enzymatic detergent within the tray. As such, the person performing the cleaning need only obtain a kit, pull off the pull-away lid, and he/she is ready for cleaning.

While this pre-cleaning kit remedies many of the problems associated with prior art cleaning techniques, it does still suffer from a number of deficiencies. For example, because of the generally flat configuration of the tray, it is relatively easy to inadvertently spill the enzymatic detergent as it is being suctioned into the endoscope channel. This problem is exacerbated because a relatively large opening is defined by the top of the shallow tray when the pull-away lid is removed. The generally flat configuration of the tray also makes it difficult for all of the enzymatic detergent to be suctioned out of the tray without requiring that the tray be tilted, which may be difficult to accomplish by a single person as he/she is trying to handle the endoscope.

What is desired, therefore, is an endoscope pre-cleaning kit which includes all of the elements necessary for an initial bedside cleaning of an endoscope, which requires little labor in preparing for the initial cleaning, which is configured such that it is not relatively easy to inadvertently spill enzymatic detergent as it is being suctioned into an endoscope channel, which facilitates the suctioning of all enzymatic detergent contained as part of the kit, and which includes a relatively small opening through which enzymatic detergent is suctioned.

SUMMARY OF THE INVENTION

Accordingly, it is an object of the present invention to provide an endoscope pre-cleaning kit which includes all of the elements necessary for an initial bedside cleaning of an endoscope.

Another object of the present invention is to provide an endoscope pre-cleaning kit having the above characteristics and which requires little labor in preparing for the initial cleaning.

A further object of the present invention is to provide an endoscope pre-cleaning kit having the above characteristics and which is configured such that it is not relatively easy to inadvertently spill enzymatic detergent as it is being suctioned into an endoscope channel.

Still another object of the present invention is to provide an endoscope pre-cleaning kit having the above characteristics and which facilitates the suctioning of all enzymatic detergent contained as part of the kit.

Yet a further object of the present invention is to provide an endoscope pre-cleaning kit having the above characteristics and which includes a relatively small opening through which enzymatic detergent is suctioned.

These and other objects of the present invention are achieved, in accordance with one embodiment of the present invention, by provision of an endoscope pre-cleaning kit having a sealed, flexible pouch having front and back sidewall panels and a bottom gusset panel. The sidewall panels are superimposed over one another and sealed together proximate to their top and side peripheral edges to define a top seal and two opposing side seals. The sidewall panels are sealed to the bottom gusset panel proximate to their bottom peripheral edges to define a gusseted bottom portion such that the pouch is adapted to stand upright. The kit also includes a pre-diluted detergent contained within the pouch, and an absorbent pad adapted to absorb a portion of the detergent. The pouch includes a portion adapted to be opened in order to access the detergent.

In some embodiments, the detergent comprises an enzymatic detergent. In some embodiments, the absorbent pad is disposed within the pouch. In some embodiment, the absorbent pad is attached to an outside of the pouch. In some embodiments, the pouch is taller than it is wide.

In some embodiments, the portion adapted to be opened comprises at least one weakened line in the front and back sidewall panels. In certain of these embodiments, the at least one weakened line in the front and back sidewall panels is disposed below the top peripheral edges of the front and back sidewall panels such that the top seal is adapted to be torn away before cleaning of the endoscope. In certain embodiments, the at least one weakened line in the front and back sidewall panels is disposed in an upper corner of the front and back sidewall panels such that a portion of the top seal and a portion of one of the side seals is adapted to be torn away before cleaning of the endoscope.

In some embodiments, the portion adapted to be opened comprises a hole in one of the front and back sidewall panels. In certain of these embodiments, the hole is covered by a frangible material adapted to be punctured before cleaning of the endoscope. In certain embodiments, the hole is covered by a pull-away tab adapted to be at least partially removed before cleaning of the endoscope. In some embodiments, the portion adapted to be opened comprises a weakened area of the top seal adapted to allow the front and back sidewall panels to be pulled apart from each other along at least a portion of the top seal.

In accordance with another embodiment of the present invention, an endoscope pre-cleaning kit includes a sealed, flexible pouch comprising front and back sidewall panels superimposed over one another and sealed together proximate to at least their top and side peripheral edges to define a top seal and two opposing side seals, the pouch being adapted to stand upright. The kit also includes a pre-diluted detergent contained within the pouch, and an absorbent pad adapted to absorb a portion of the detergent. The pouch includes at least one weakened line in the front and back sidewall panels adapted to allow access to the detergent.

In some embodiments, the at least one weakened line in the front and back sidewall panels is disposed below the top peripheral edges of the front and back sidewall panels such that the top seal is adapted to be torn away before cleaning of the endoscope. In some embodiments, the at least one weakened line in the front and back sidewall panels is disposed in an upper corner of the front and back sidewall panels such that a portion of the top seal and a portion of one of the side seals is adapted to be torn away before cleaning of the endoscope.

In some embodiments, the pouch further includes a hole in one of the front and back sidewall panels in order to allow access to the detergent. In certain of these embodiments, the hole is covered by a frangible material adapted to be punctured before cleaning of the endoscope. In certain embodiments, the hole is covered by a pull-away tab adapted to be at least partially removed before cleaning of the endoscope.

In accordance with a further embodiment of the present invention, an endoscope pre-cleaning kit includes a sealed, flexible pouch comprising front and back sidewall panels superimposed over one another and sealed together proximate to at least their top and side peripheral edges to define a top seal and two opposing side seals, the pouch being adapted to stand upright. The kit also includes a pre-diluted detergent contained within the pouch, and an absorbent pad adapted to absorb a portion of the detergent. The pouch includes a hole in one of the front and back sidewall panels adapted to allow access to the detergent.

In some embodiments, the hole is covered by a frangible material adapted to be punctured before cleaning of the endoscope. In some embodiments, the hole is covered by a pull-away tab adapted to be at least partially removed before cleaning of the endoscope.

In some embodiments, the pouch further includes at least one weakened line in the front and back sidewall panels adapted to allow access to the detergent. In certain of these embodiments, the at least one weakened line in the front and back sidewall panels is disposed below the top peripheral edges of the front and back sidewall panels such that the top seal is adapted to be torn away before cleaning of the endoscope. In certain embodiments, the at least one weakened line in the front and back sidewall panels is disposed in an upper corner of the front and back sidewall panels such that a portion of the top seal and a portion of one of the side seals is adapted to be torn away before cleaning of the endoscope. In some embodiments, the top seal includes a weakened area adapted to allow the front and back sidewall panels to be pulled apart from each other along at least a portion of the top seal in order to allow access to the detergent.

In accordance with another embodiment of the present invention, an endoscope pre-cleaning kit includes a sealed, flexible pouch comprising front and back sidewall panels superimposed over one another and sealed together proximate to at least their top and side peripheral edges to define a top seal and two opposing side seals, the pouch being adapted to stand upright. The kit also includes a pre-diluted detergent contained within the pouch, and an absorbent pad adapted to absorb a portion of the detergent. The top seal includes a weakened area adapted to allow the front and back sidewall panels to be pulled apart from each other along at least a portion of the top seal in order to allow access to the detergent.

In some embodiments, the pouch further includes a hole in one of the front and back sidewall panels in order to allow access to the detergent. In certain of these embodiments, the hole is covered by a frangible material adapted to be punctured before cleaning of the endoscope. In certain embodiments, the hole is covered by a pull-away tab adapted to be at least partially removed before cleaning of the endoscope.

The invention and its particular features and advantages will become more apparent from the following detailed description considered with reference to the accompanying drawings.

DETAILED DESCRIPTION OF AN EMBODIMENT OF THE INVENTION

Figure 1:
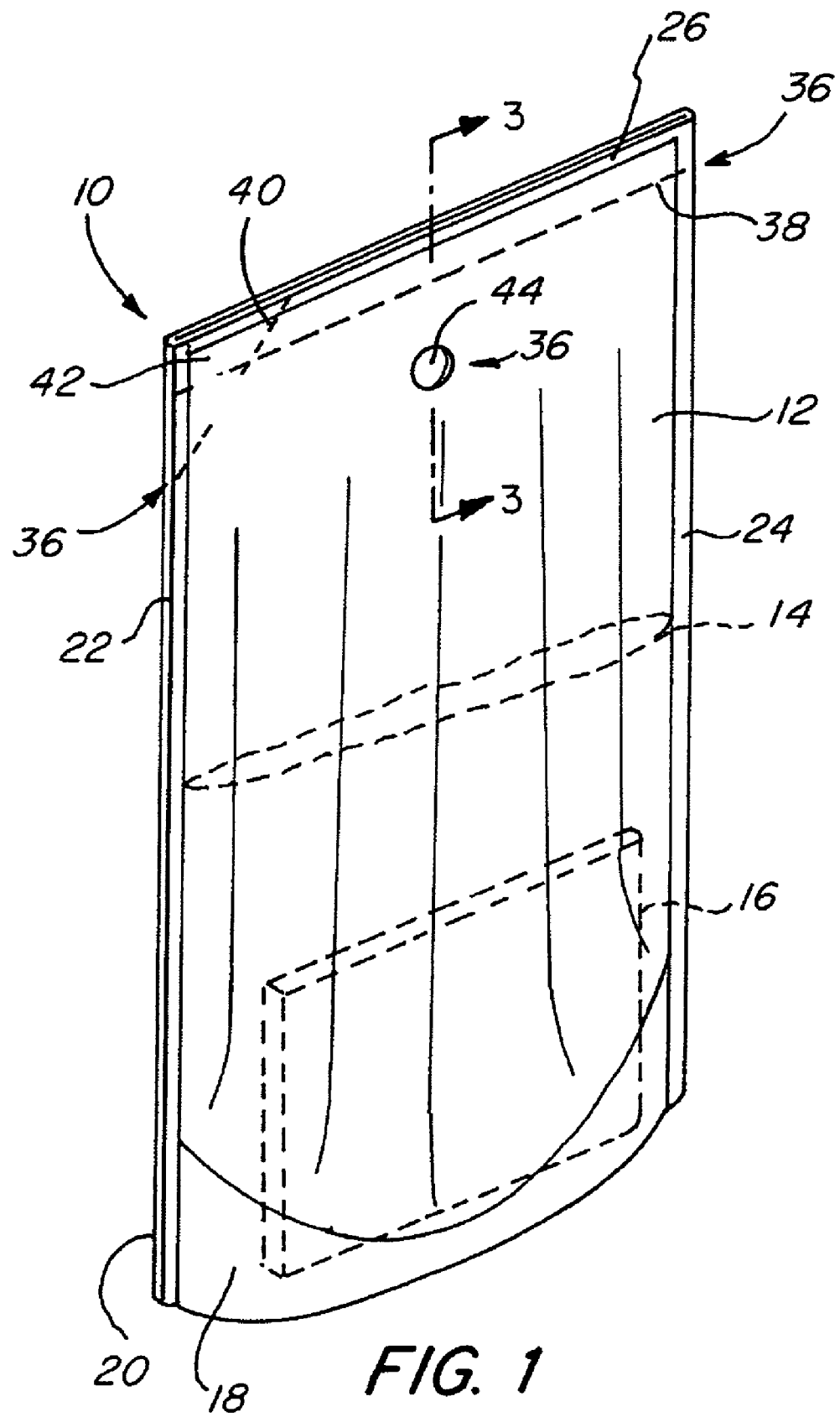
FIG. 1 is a side isometric view of an endoscope pre-cleaning kit in accordance with an embodiment of the present invention.

Referring first to FIG. 1, an endoscope pre-cleaning kit 10 generally includes a sealed, flexible pouch 12, a pre-diluted detergent 14 contained within the pouch 12, and an absorbent pad 16 adapted to absorb a portion of the detergent.

Figure 2:
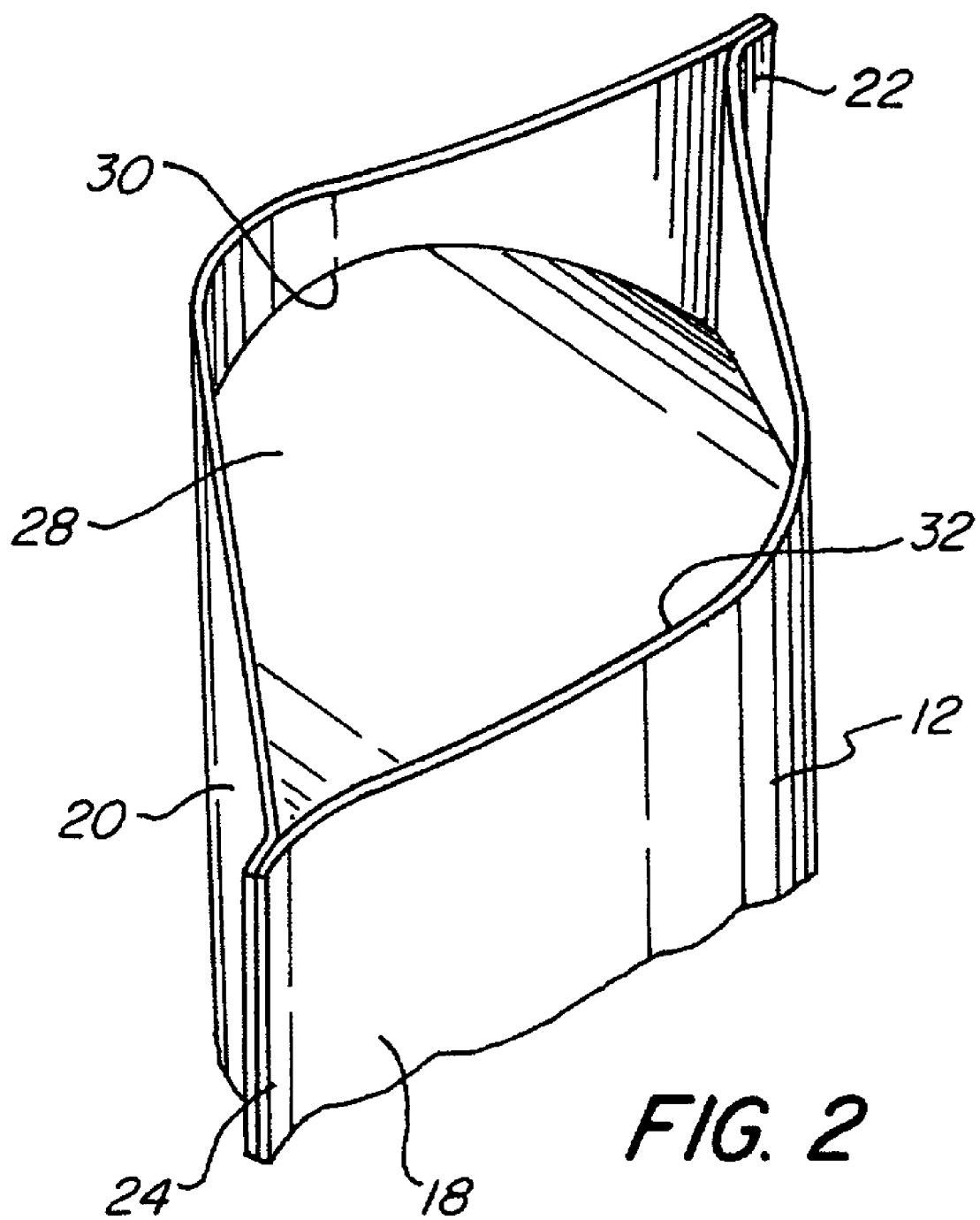
FIG. 2 is a bottom isometric view of a portion of the endoscope pre-cleaning kit shown in FIG. 1.

Pouch 12 includes flexible sidewall panels 18, 20 that are superimposed over one another and sealed together, e.g., heat-sealed, along side peripheral edges to form side seals 22, 24, and along a top peripheral edge to form top seal 26. Bottom peripheral edges of sidewall panels 18, 20, can also be sealed to one another to form a bottom seal (not shown in Figures) and thereby complete a closed pouch structure. However, in the particularly preferred embodiment of the present invention illustrated in FIGS. 1 and 2, bottom gusset panel 28 is attached to the inner surface of sidewalls 18, 20 in a bottom portion of pouch 12 along generally arcuate seal lines 30, 32, respectively, and preferably also in the area therebelow. This allows the pouch 12 to stand upright without being supported. The portion of bottom gusset panel 28 above seal lines 30, 32 is not attached to the inner surface of sidewalls 18, 20 such that a midsection of gusset 28 is free and defines a bottom of pouch 12, as best seen in FIG. 2. Preferably, pouch 12 is taller than it is wide such that detergent 14 is inhibited from splashing out of pouch 12.

Sidewall panels 18, 20 can be made from a wide variety of materials that meet certain preferred specifications. For example, sidewalls 18, 20 are preferably thin to reduce the amount of material used and the associated cost, while being sufficiently thick and tough enough to resist punctures and leaks caused by abrasion and tough handling. In addition, sidewalls 18, 20 are preferably made of materials that are rigid enough to allow a user to grasp the pouch 12 without significantly deforming or collapsing the pouch's sidewall panels, because deforming or collapsing would make pouch 12 difficult to grasp and/or to stand upright. Sidewalls 18, 20 are also preferably selected from materials that can be easily handled, formed, and sealed together, preferably by heat-sealing, in a high-speed manufacturing setting by using a high-speed form, fill, and seal apparatus. Finally, sidewalls 18, 20 are preferably made of a material or a laminate combination of materials that provides an adequate barrier against moisture, oxygen, and light which may adversely affect the performance or quality of the product contained within the pouch, particularly over an extended period of time.

Bottom gusset panel 28 of pouch 12 is also preferably made from a material that has the aforementioned properties in addition to being slightly more flexible than sidewalls 18, 20 so that gusset 28 will readily drop downward and expand when pouch 12 is filled with a fluid as previously described herein.

The detergent 14 is preferably an enzymatic detergent, which is particularly adapted to loosen and/or facilitate the removal of debris on or within the endoscope to be cleaned. Specifically, detergent 14 should be effective to dissolve one or more of the following: blood, fat, protein, tissue, and other forms of organic protenacious materials. Detergent 14 may, for example, contain one or more of the following: protease, amylase, carbohydrase and lipase. Preferably, detergent 14 is pH neutral, or at lease close thereto, so that it will not rust or damage stainless steel instruments and so that it will not adversely affect delicate endoscopic instruments. Kit 10 should include a sufficient amount of detergent 14 to allow absorbent pad 16 to be soaked, and also for the endoscope channel to be sufficiently cleaned by suctioning detergent 14, optionally being alternated with air, therethrough. It has been found that providing approximately 8 oz. of detergent 14 provides adequate results.

Figure 4:
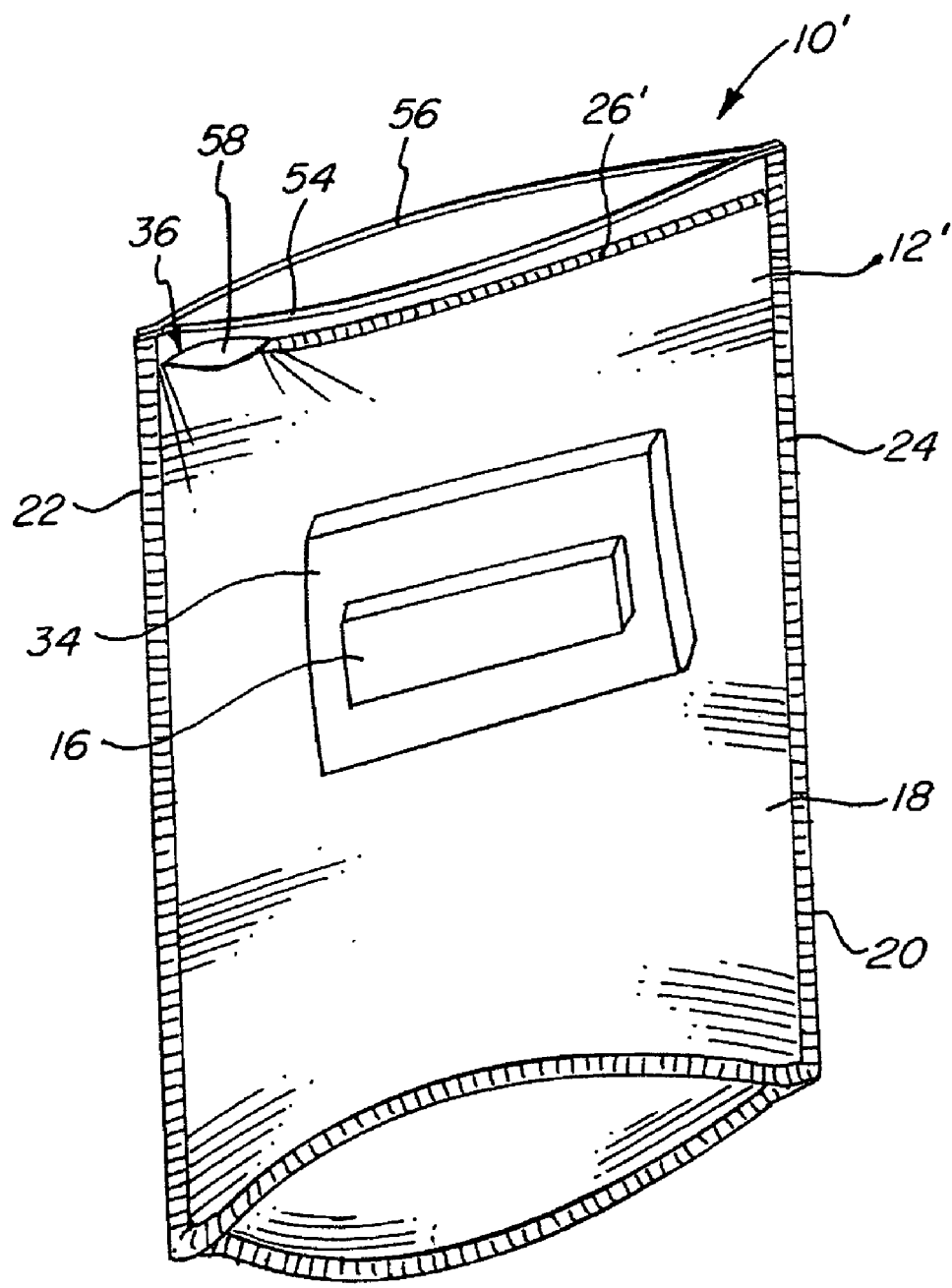
FIG. 4 is a side isometric view of an endoscope pre-cleaning kit in accordance with another embodiment of the present invention.

Absorbent pad 16 may be formed from a sponge material (natural or synthetic), a foam material, a cloth material, or any of numerous other absorbent materials. It has been found that forming absorbent pad 16 of a foam material that is generally flat on one side and has a series of contoured ridges on the other provides adequate results. Such pads are available from Cygnus Medical of Branford, Conn. under the name "Krinkle Pad". Pad 16 may be provided within pouch 12 in a presoaked condition (as shown in FIG. 1), or it may be provided attached to an outside of pouch 12, for example, contained within a bag 34 attached to an outside of pouch 12 (as shown in FIG. 4). In the latter case, pad 16 may be pre-soaked with detergent within bag 34 and/or pad 16 may require soaking in detergent 14 contained within pouch 12, 12'.

The pouch 12 includes a portion 36 adapted to be opened in order to access the detergent 14 in order to suck the detergent through the channel of the endoscope being cleaned and/or in order to reach and/or soak absorbent pad 16. Portion 36 may comprise a line of weakness 38 that extends laterally across both sidewalls 18, 20 in close proximity to, but below, top peripheral seal 26. Weakness line 38 may be formed by, for example, perforating or scoring sidewalls 18, 20 with a laser or knife either individually before sidewalls 18, 20 are sealed together, or collectively after they have been sealed together. One or both ends of weakness line 38 preferably terminates with a notch (not shown), which provides a stress concentration and aids in starting a tear along weakness line 38 when pouch 12 is opened by a consumer. As will be appreciated, weakness line 38 allows a relatively large opening to be created, such that pad 16 can be inserted into and removed from within pouch 12.

In addition to, or instead of, weakness line 38 being provided, a weakness line 40 may be provided spanning a corner 42 of pouch 12 from one of side peripheral seals 22, 24 to top peripheral seal 26. Weakness line 40 may be created in a manner similar to weakness line 38, as described above, and may also include notches. Weakness line 40 may be used in order to insert endoscope into pouch 12 in order to suction out detergent 14. Because the opening created by removing corner 42 along weakness line 40 is relatively small, the risk of substantial spillage of detergent 14 is reduced. However, it would be difficult to insert or remove pad 16 using this opening.

In addition to, or instead of, weakness lines 38, 40 being provided, a hole 44 may be provided in one or more of sidewalls 18, 20. Hole 44 may be used in order to insert endoscope into pouch 12 in order to suction out detergent 14. Because hole 44 is relatively small, the risk of substantial spillage of detergent 14 is reduced. However, it would be difficult to insert or remove pad 16 using hole 44. Hole 44 should be sized to receive endoscopes of typical sizes. For example, hole 44 may have a diameter of about 12 mm in order to receive typical endoscopes having diameters of about 10 mm.

Figure 3A:
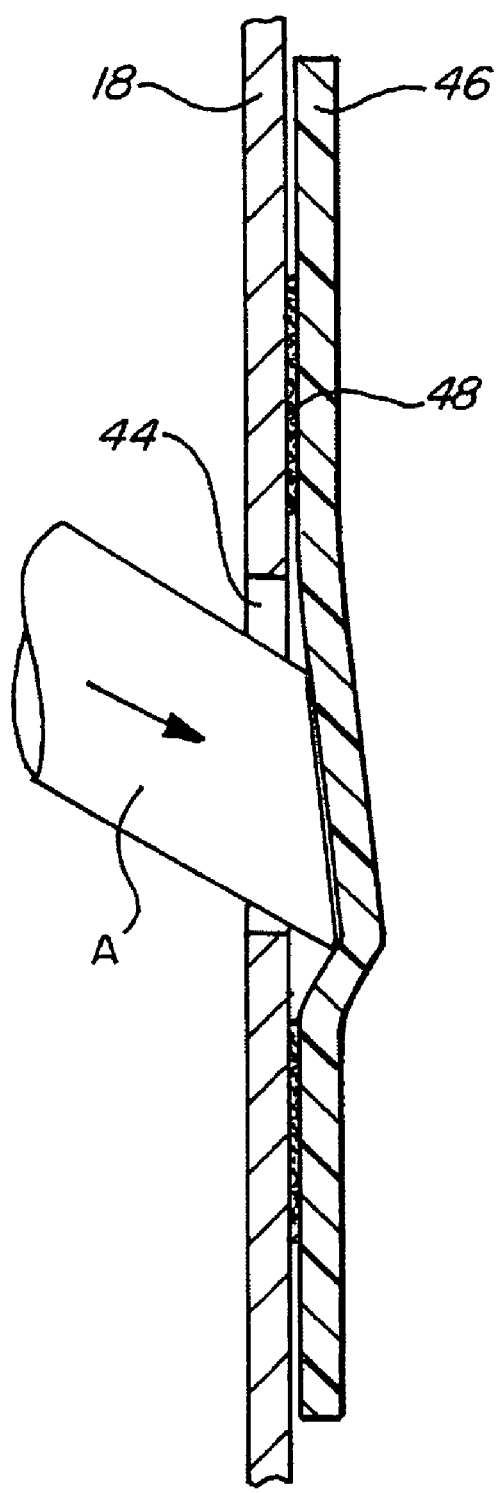
FIG. 3A is a partially cross-sectional view, taken along line 3-3, showing in more detail a particular embodiment of the endoscope pre-cleaning kit shown in FIG. 1.
Figure 3B:
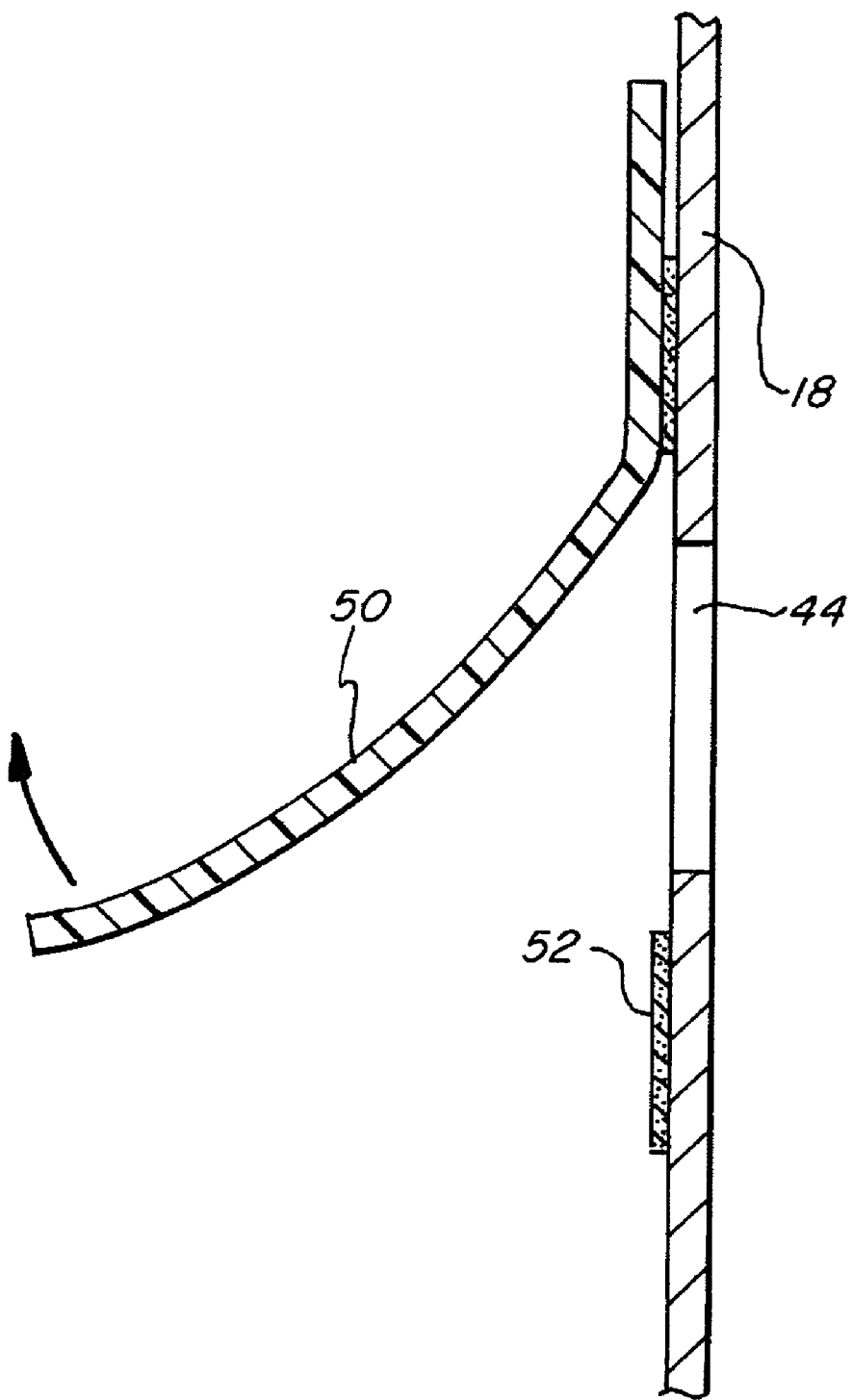
FIG. 3B is a partially cross-sectional view, taken along line 3-3, showing in more detail another particular embodiment of the endoscope pre-cleaning kit shown in FIG. 1.

In order to prevent detergent 14 from leaking out from pouch, hole 44 may be sealed by a frangible material 46 adapted to be punctured by an endoscope being cleaned or the like (designated by reference character A in FIG. 3A). Frangible material 46 may be disposed within pouch 12 and attached to the area surrounding hole 44 by an adhesive 48 or the like. Alternately, as shown in FIG. 3B, hole 44 may be covered by a pull-away tab 50 or the like attached to the outside of pouch 12 in an area surrounding hole 44 by way of an adhesive 52. Tab 50 may be removed before an endoscope or the like is inserted through hole 44.

Referring now to FIG. 4, another embodiment of a kit 10' in accordance with the present invention is shown. In this embodiment, pouch 12' is formed such that the top peripheral seal 26' is formed below the upper edges 54, 56 of sidewalls 18, 20, and the top peripheral seal 26' is formed such that it is partially or totally unsealable. This, a user may grasp the upper edges 54, 56 of sidewalls 18, 20 and by pulling them apart, create an opening 58 within pouch 12'. The opening 58 may be relatively small (e.g., just large enough to insert the endoscope to be cleaned into pouch 12') or may be relatively large (e.g., so that absorbent pad 16 may be inserted into and removed from pouch 12').

The present invention, therefore, provides an endoscope pre-cleaning kit which includes all of the elements necessary for an initial bedside cleaning of an endoscope, which requires little labor in preparing for the initial cleaning, which is configured such that it is not relatively easy to inadvertently spill enzymatic detergent as it is being suctioned into an endoscope channel, which facilitates the suctioning of all enzymatic detergent contained as part of the kit, and which includes a relatively small opening through which enzymatic detergent is suctioned.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An endoscope pre-cleaning kit comprising:

a sealed, flexible pouch comprising front and back sidewall panels and a bottom gusset panel, the sidewall panels being superimposed over one another and sealed together proximate to their top and side peripheral edges to define a top seal and two opposing side seals, the sidewall panels being sealed to the bottom gusset panel proximate to bottom peripheral edges of the sidewall panels to define a gusseted bottom portion such that said pouch is adapted to stand upright;

a pre-diluted detergent contained within said pouch; and an absorbent pad adapted to absorb a portion of said detergent, said absorbent pad is disposed within said pouch or said absorbent pad is attached to an outside of said pouch;

wherein said pouch includes a portion adapted to be opened in order to access said detergent;

wherein the portion adapted to be opened comprises at least one weakened line in the front and back sidewall panels; and wherein the pouch is capable of standing upright before it is opened to access said detergent.

2. The endoscope pre-cleaning kit of claim 1 wherein said detergent comprises an enzymatic detergent.

3. The endoscope pre-cleaning kit of claim 1 wherein said pouch is taller than it is wide.

4. The endoscope pre-cleaning kit of claim 1 wherein the at least one weakened line in the front and back sidewall panels is disposed below the top peripheral edges of the front and back sidewall panels such that the top seal is adapted to be torn away before cleaning of the endoscope.

5. The endoscope pre-cleaning kit of claim 1 wherein the at least one weakened line in the front and back sidewall panels is disposed in an upper corner of the front and back sidewall panels such that a portion of the top seal and a portion of one of the side seals is adapted to be torn away before cleaning of the endoscope.

6. The endoscope pre-cleaning kit of claim 1 wherein the portion adapted to be opened comprises a hole in one of the front and back sidewall panels.

7. The endoscope pre-cleaning kit of claim 6 wherein the hole is covered by a frangible material adapted to be punctured before cleaning of the endoscope.

8. The endoscope pre-cleaning kit of claim 6 wherein the hole is covered by a pull-away tab adapted to be at least partially removed before cleaning of the endoscope.

9. The endoscope pre-cleaning kit of claim 1 wherein the portion adapted to be opened comprises a weakened area of the top seal adapted to allow the front and back sidewall panels to be pulled apart from each other along at least a portion of the top seal.

10. An endoscope pre-cleaning kit comprising:

a sealed, flexible pouch comprising front and back sidewall panels superimposed over one another and sealed together proximate to at least top and side peripheral edges of the front and back sidewall panels to define a top seal and two opposing side seals, said pouch being adapted to stand upright;

a pre-diluted detergent contained within said pouch; and an absorbent pad adapted to absorb a portion of said detergent, said absorbent pad is disposed within said pouch or said absorbent pad is attached to an outside of said pouch;

wherein said pouch includes at least one weakened line in the front and back sidewall panels adapted to allow access to said detergent; and wherein the pouch is capable of standing upright before it is opened to access said detergent.

11. The endoscope pre-cleaning kit of claim 10 wherein the at least one weakened line in the front and back sidewall panels is disposed below the top peripheral edges of the front and back sidewall panels such that the top seal is adapted to be torn away before cleaning of the endoscope.

12. The endoscope pre-cleaning kit of claim 10 wherein the at least one weakened line in the front and back sidewall panels is disposed in an upper corner of the front and back sidewall panels such that a portion of the top seal and a portion of one of the side seals is adapted to be torn away before cleaning of the endoscope.

13. The endoscope pre-cleaning kit of claim 10 wherein said pouch further includes a hole in one of the front and back sidewall panels in order to allow access to said detergent.

14. The endoscope pre-cleaning kit of claim 13 wherein the hole is covered by a frangible material adapted to be punctured before cleaning of the endoscope.

15. The endoscope pre-cleaning kit of claim 13 wherein the hole is covered by a pull-away tab adapted to be at least partially removed before cleaning of the endoscope.

16. An endoscope pre-cleaning kit comprising:

a sealed, flexible pouch comprising front and back sidewall panels superimposed over one another and sealed together proximate to at least top and side peripheral edges of the front and back sidewall panels to define a top seal and two opposing side seals, said pouch being adapted to stand upright;

a pre-diluted detergent contained within said pouch; and an absorbent pad adapted to absorb a portion of said detergent, said absorbent pad is disposed within said pouch or said absorbent pad is attached to an outside of said pouch;

wherein said pouch includes a hole in one of the front and back sidewall panels adapted to allow access to said detergent;

wherein said pouch further includes at least one weakened line in the front and back sidewall panels adapted to allow access to said detergent, and wherein the pouch is capable of standing upright before it is opened to access said detergent.

17. The endoscope pre-cleaning kit of claim 16 wherein the hole is covered by a frangible material adapted to be punctured before cleaning of the endoscope.

18. The endoscope pre-cleaning kit of claim 16 wherein the hole is covered by a pull-away tab adapted to be at least partially removed before cleaning of the endoscope.

19. The endoscope pre-cleaning kit of claim 16 wherein the at least one weakened line in the front and back sidewall panels is disposed below the top peripheral edges of the front and back sidewall panels such that the top seal is adapted to be torn away before cleaning of the endoscope.

20. The endoscope pre-cleaning kit of claim 16 wherein the at least one weakened line in the front and back sidewall panels is disposed in an upper corner of the front and back sidewall panels such that a portion of the top seal and a portion of one of the side seals is adapted to be torn away before cleaning of the endoscope.

21. The endoscope pre-cleaning kit of claim 16 wherein the top seal includes a weakened area adapted to allow the front and back sidewall panels to be pulled apart from each other along at least a portion of the top seal in order to allow access to said detergent.

* * * * *